(12) United States Patent
Charmot et al.

(10) Patent No.: US 8,409,561 B2
(45) Date of Patent: Apr. 2, 2013

(54) METHODS AND COMPOSITIONS FOR TREATMENT OF ION IMBALANCES (75) Inventors: Dominique Charmot, Campbell, CA (US); Han-Ting Chang, Livermore, CA (US); Mingjun Liu, Campbell, CA (US); Futian Liu, Sunnyvale, CA (US); Gerrit Klaerner, Los Gatos, CA (US)

(73) Assignee: Relypsa, Inc., Redwood City, CA (US)

( * ) Notice: Subject to any disclaimer, the term of this patent is extended or adjusted under 35 U.S.C. 154(b) by 115 days.

(21) Appl. No.: 12/857,264

(22) Filed: Aug. 16, 2010

(65) Prior Publication Data

US 2011/0033505 A1 Feb. 10, 2011

Related U.S. Application Data (60) Division of application No. 11/095,760, filed on Mar. 30, 2005, now Pat. No. 7,776,319, which is a continuation-in-part of application No. 10/965,274, filed on Oct. 13, 2004, now Pat. No. 7,488,495, which is a continuation-in-part of application No. 10/813,872, filed on Mar. 30, 2004, now Pat. No. 8,282,960, and a continuation-in-part of application No. 10/814,527, filed on Mar. 30, 2004, now Pat. No. 7,854,924, and a continuation-in-part of application No. 10/814,749, filed on Mar. 30, 2004, now Pat. No. 8,192,758.

(51) Int. Cl.
*A61K 31/74* (2006.01)
*A61K 31/765* (2006.01)
*A61K 31/785* (2006.01)
*A61K 9/14* (2006.01)
*A61P 3/12* (2006.01)
*A61P 9/12* (2006.01)
*A61P 13/12* (2006.01)

(52) U.S. Cl. ............... 424/78.1; 424/78.12; 424/490; 424/497; 514/838; 514/869; 514/870; 514/893

(58) Field of Classification Search ............... 424/78.1, 424/490, 497; 514/838, 869, 870, 893
See application file for complete search history.

(56) References Cited

U.S. PATENT DOCUMENTS

| | | | |
|---|---|---|---|
| 2,611,730 A | 9/1952 | Heming et al. | |
| 2,909,462 A | 10/1959 | Warfield et al. | |
| 3,499,960 A | 3/1970 | Macek et al. | |
| 3,974,272 A | 8/1976 | Polli et al. | |
| 4,143,130 A | 3/1979 | Imondi et al. | |
| 4,380,590 A | 4/1983 | Chong | |
| 4,470,975 A | 9/1984 | Berger et al. | |
| 4,605,701 A | 8/1986 | Harada et al. | |
| 4,747,881 A | 5/1988 | Shaw et al. | |
| 4,837,015 A | 6/1989 | Olsen | |
| 4,902,501 A | 2/1990 | Bandi et al. | |
| 5,051,253 A | 9/1991 | Lloyd-Jones et al. | |
| 5,091,175 A | 2/1992 | Imondi et al. | |
| 5,141,927 A | 8/1992 | Krotkiewski | |
| 5,186,937 A | 2/1993 | Sparks et al. | |
| 5,281,631 A | 1/1994 | Horwitz et al. | |
| 5,374,422 A | 12/1994 | St. Pierre et al. | |
| 5,487,888 A | 1/1996 | Mandeville, III et al. | |
| 5,607,669 A | 3/1997 | Mandeville, III et al. | |
| 5,618,530 A | 4/1997 | Mandeville, III et al. | |
| 5,633,344 A | 5/1997 | Figuly | |
| 5,667,775 A | 9/1997 | Holmes-Farley et al. | |
| 5,679,717 A | 10/1997 | Mandeville, III et al. | |
| 5,693,675 A | 12/1997 | Mandeville, III et al. | |
| 5,702,696 A | 12/1997 | Mandeville, III et al. | |
| 5,718,920 A | 2/1998 | Notenbomer | |
| 5,824,339 A | 10/1998 | Shimizu et al. | |
| 5,935,599 A | 8/1999 | Dadey | |
| 6,294,163 B1 | 9/2001 | Dhal et al. | |
| 6,558,665 B1 | 5/2003 | Cohen et al. | |
| 6,881,484 B2 | 4/2005 | Kataoka et al. | |
| 7,429,394 B2 | 9/2008 | Charmot et al. | |
| 7,488,495 B2 | 2/2009 | Charmot et al. | |
| 8,192,758 B2 * | 6/2012 | Charmot et al. | 424/483 |
| 8,282,960 B2 * | 10/2012 | Charmot et al. | 424/490 |
| 2002/0054903 A1 | 5/2002 | Tyler et al. | |
| 2002/0146386 A1 | 10/2002 | Simon et al. | |
| 2003/0027789 A1 | 2/2003 | Yamaoka et al. | |
| 2003/0065090 A1 | 4/2003 | Kelly et al. | |
| 2004/0166156 A1 | 8/2004 | Tyler et al. | |
| 2005/0036983 A1 | 2/2005 | Simon et al. | |
| 2005/0220750 A1 | 10/2005 | Robert et al. | |

FOREIGN PATENT DOCUMENTS

| | | |
|---|---|---|
| EP | 0 040 590 A2 | 11/1981 |
| EP | 0 349 453 A1 | 1/1990 |
| EP | 0 730 494 B1 | 2/1998 |
| JP | 10-59851 A | 3/1998 |
| JP | 10-130154 A | 5/1998 |
| WO | 82/00257 A1 | 2/1982 |
| WO | 92/10522 A1 | 6/1992 |
| WO | 94/27619 A1 | 12/1994 |
| WO | 95/14531 A1 | 6/1995 |
| WO | 97/49387 A1 | 12/1997 |
| WO | 97/49736 A2 | 12/1997 |
| WO | 00/40224 A1 | 7/2000 |
| WO | 01/51063 A1 | 7/2001 |
| WO | 02/12160 A1 | 2/2002 |

(Continued)

OTHER PUBLICATIONS

HCAPLUS Abstract 2002:221441 (2002).*

(Continued)

*Primary Examiner* — John Pak
(74) *Attorney, Agent, or Firm* — Senniger Powers LLP (57) ABSTRACT The present invention provides methods and compositions for the treatment of ion imbalances. In particular, the invention provides compositions comprising sodium-binding polymers and pharmaceutical compositions thereof. Methods of use of the polymeric and pharmaceutical compositions for therapeutic and/or prophylactic benefits are disclosed herein. Examples of these methods include the treatment of hypertension, chronic heart failure, end stage renal disease, liver cirrhosis, chronic renal insufficiency, fluid overload, or sodium overload.

16 Claims, 2 Drawing Sheets

FOREIGN PATENT DOCUMENTS

| WO | 02/40039 A2 | 5/2002 |
|---|---|---|
| WO | 02/062356 A2 | 8/2002 |
| WO | 2005/065291 A2 | 7/2005 |

OTHER PUBLICATIONS

Agarwal, R., et al., "Pathophysiology of Potassium Absorption and Secretion by the Human Intestine," Gastroenterology, Aug. 1994, pp. 548-571, vol. 107, No. 2.

Berlyne, G. M., et al., "Cation Exchange Resins in Hyperkalaemic Renal Failure," Israel J. Med. Sci., Jan.-Feb. 1967, pp. 45-52, vol. 3, No. 1.

Chourasia, M. K., et al., "Pharmaceutical Approaches to Colon Targeted Drug Delivery Systems," J. Pharm. Pharmaceut. Sci., 2003, pp. 33-66, vol. 6, No. 1.

Coli, L., et al., "Phosphate Removal by Resin Hemoperfusion Efficacy and Biocompatibility of a New Exchange Resin," Biomaterials, Artificial Cells, and Immobilization Biotechnology, 1992, pp. 1153-1163, vol. 20, No. 5.

Corcoran, A. C., et al., "Controlled Observations on the Effect of Low Sodium Dietotherapy in Essential Hypertension," Circulation, Jan. 1951, pp. 1-16, vol. 3, No. 1.

Cuna, M., et al., "Controlled-Release Liquid Suspensions Based on Ion-Exchange Particles Entrapped Within Acrylic Microcapsules," International Journal of Pharmaceutics, Apr. 20, 2000, pp. 151-158, vol. 199, No. 2.

Dai, J., et al., "Controlling Ion Transport Through Multilayer Polyelectrolyte Membranes by Derivatization with Photolabile Functional Groups," Macromolecules, 2002, pp. 3164-3170, vol. 35, No. 8.

Danowski, T.S., et al., "Changes in Fecal and Serum Constituents During Ingestion of Cation and Anion Exchangers," Annals New York Academy of Sciences, 1953, pp. 273-279, vol. 57, No. 3.

Emerson, K., Jr., et al., "The Role of the Gastro-Intestinal Tract in the Adaptation of the Body to the Prevention of Sodium Depletion by Cation Exchange Resins," Annals New York Academy of Sciences, 1953, pp. 280-290, vol. 57, No. 3.

Emmett, M., et al., "Effect of Three Laxatives and a Cation Exchange Resin on Fecal Sodium and Potassium Excretion," Gastroenterology, Mar. 1995, pp. 752-760, vol. 108, No. 3.

Estrela-Lopis, I., et al., "SANS Studies of Polyelectrolyte Multilayers on Colloidal Templates," Langmuir, 2002, pp. 7861-7866, vol. 18, No. 21.

Evans, B. M., et al., "Ion-Exchange Resins in the Treatment of Anuria," The Lancet, Oct. 17, 1953, pp. 791-795, vol. 265, No. 6790.

Field, H., Jr., et al., "Electrolyte Changes in Ileal Contents and in Feces During Restriction of Dietary Sodium With and Without the Administration of Cation-Exchange Resin," Circulation, Oct. 1955, pp. 625-629, vol. 12, No. 4.

Field, H., Jr., et al., "Mechanisms Regulating the Retention of Sodium in the Feces by Cation-Exchange Resin: Release of Base from the Resin by Bacterial Fermentation in the Terminal Ileum," J. Lab. & Clin. Med., Feb. 1958, pp. 178-184, vol. 51, No. 2.

Forrest, M. L., et al., "A Degradable Polyethylenimine Derivative with Low Toxicity for Highly Efficient Gene Delivery," Bioconjugate Chem., Sep.-Oct. 2003, pp. 934-940, vol. 14, No. 5.

Friedman, E. A., "Sorbent Therapy in Uremia," Clinical Aspects of Uremia and Dialysis, Chapter 24, 1976, pp. 671-687.

Friedman, E. A., et al., "Combined Oxystarch-Charcoal Trial in Uremia: Sorbent-Induced Reduction in Serum Cholesterol," Kidney International, Dec. 1976, pp. S273-S276, vol. 7.

Fourman, P., "Capacity of a Cationic Exchange Resin ("Zeo-Karb 225") In Vivo," British Medical Journal, Mar. 7, 1953, pp. 544-546, vol. 1, No. 4809.

Gerstman, B. B., et al., "Use of Sodium Polystyrene Sulfonate in Sorbitol in the United States, 1985-1989," American Journal of Kidney Disease, Nov. 1991, pp. 619-621, vol. 18, No. 5.

Greenman, L., et al., "Biochemical Changes Accompanying the Ingestion of a Carboxylic Cation Exchanger in the Hydrogen, Ammonium, Sodium, Potassium, or Calcium Form," J. Clin. Invest., Sep. 1951, pp. 995-1008, vol. 30, No. 9.

Gruy-Kapral, C., et al., "Effect of Single Dose Resin-Cathartic Therapy on Serum Potassium Concentration in Patients with End-Stage Renal Disease," J. Am. Soc. Nephrol., Oct. 1998, pp. 1924-1930, vol. 9, No. 10.

Harthon, J. G. L., et al., "A Case of Uremia and Hyperpotassemia Treated with Sulphonic Cation-Exchange Resin," Acta Medica Scandinavica, 1952, pp. 230-236, vol. 144, No. 3.

Heming, A. E., et al., "Considerations in the Selection of Cation Exchange Resins for Therapeutic Use," Annals New York Academy of Sciences, Nov. 11, 1953, pp. 239-251, vol. 57, No. 3.

Ichikawa, H., et al., "Use of Ion-Exchange Resins to Prepare 100 μm-Sized Microcapsules with Prolonged Drug-Release by the Wurster Process," International Journal of Pharmaceutics, Mar. 23, 2001, pp. 67-76, vol. 216, No. 1-2.

Imondi, A. R., et al., "Gastrointestinal Sorbents for the Treatment of Uremia. I. Lightly Cross-Linked Carboxyvinyl Polymers," Ann. Nutr. Metabol., 1981, pp. 311-319, vol. 25, No. 5.

Irwin, L., et al., "The Effect of a Cation Exchange Resin on Electrolyte Balance and Its Use in Edematous States," J Clin. Invest., Nov. 1949, pp. 1403-1411, vol. 28, No. 6, Part 2.

Kim, H.-J., et al., "Therapeutic Approach to Hyperkalemia," Nephron, 2002, pp. 33-40, vol. 92, Supplement 1.

Kohlstaedt, K. G., et al., "Clinical Experience with Mixtures of Anion and Cation Exchange Resins," Annals New York Academy of Sciences, Nov. 11, 1953, pp. 260-272, vol. 57, No. 3.

Koping-Hoggard, M., et al., "Chitosan as a Nonviral Gene Delivery System. Structure-Property Relationships and Characteristics Compared with Polyethylenimine in vitro and After Lung Administration in vivo," Gene Therapy, Jul. 2001, pp. 1108-1121, vol. 8, No. 14.

Mason, N. S., et al., "A New Ion Exchanger with High in vivo Sodium Capacity," Kidney International Suppl., Dec. 1985, pp. S178-S182, vol. 17.

Mateer, F. M., et al, "Sodium Restriction and Cation Exchange Resin Therapy in Nephrotic Children," J. Clin. Invest., Sep. 1951, pp. 1018-1026, vol. 30, No. 9.

McChesney, E. W., "Effects of Long-Term Feeding of Sulfonic Ion Exchange Resin on the Growth and Mineral Metabolism of Rats," Am. J. Physiol., Jun. 1954, pp. 395-400, vol. 177, No. 3.

McChesney, E. W., et al., "Some Aspects of Cation Exchange Resins as Therapeutic Agents for Sodium Removal," Annals New York Academy of Sciences, Nov. 11, 1953, pp. 252-259, vol. 57, No. 3.

Meszaros, R., et al., "Adsorption of Poly(ethyleneimine) on Silica Surfaces: Effect of pH on the Reversibility of Adsorption," Langmuir, Jun. 8, 2004, pp. 5026-5029, vol. 20, No. 12.

Moustafine, R. I., et al., "Characteristics of Interpolyelectrolyte Complexes of Eudragit E 100 With Sodium Alginate," International Journal of Pharmaceutics, Apr. 27, 2005, pp. 113-120, vol. 294, No. 1-2.

Picart, C., et al., "Microinterferometric Study of the Structure, Interfacial Potential, and Viscoelastic Properties of Polyelectrolyte Multilayer Films on a Planar Substrate," J. Phys. Chem. B, 2004, pp. 7196-7205, vol. 108, No. 22.

Root, M. A., "Comparison of the in vivo Sodium-Removing Activity of Various Types of Ion Exchange Resins in Rats," J. Lab. & Clin. Med., Sep. 1953, pp. 430-437, vol. 42, No. 3.

Ross, E. J., et al., "Observations on Cation Exchange Resins in the Small and Large Intestines," Clin. Sci., Nov. 1954, pp. 555-566, vol. 13, No. 4.

Salas-Coll, C. A., et al., "Potassium Transport Across the Distal Colon in Man," Clinical Science and Molecular Medium, Sep. 1976, pp. 287-296, vol. 51, No. 3.

Spencer, A. G., et al., "Cation Exchange in the Gastrointestinal Tract," British Medical Journal, Mar. 13, 1954, pp. 603-606, vol. 1, No. 4862.

Thies, C., "Microcapsules as Drug Delivery Devices," CRC Critical Reviews in Biomedical Engineering, 1982, pp. 335-383, vol. 8, No. 4.

Thomas, M., et al., "Cross-Linked Small Polyethylenimines: While Still Nontoxic, Deliver DNA Efficiently to Mammalian Cells in vitro and in vivo," Pharmaceutical Research, Mar. 2005, pp. 373-380, vol. 22, No. 3.

Tust, R. H., et al., "The Effects of Malethamer on the Excretion and Plasma Levels of Sodium, Potassium, and Cloride (34990)," Proc. Soc. Exp. Biol. Med., Oct. 1970, pp. 72-76, vol. 135, No. 1.

Wrong, O. M., et al., "In Vivo Dialysis of Faeces as a Method of Stool Analysis," Clinical Science, Apr. 1965, pp. 357-375, vol. 28.

Wrong, O. M., et al., "The Electrolyte Content Faeces," Proceedings of the Royal Society of Medicine, Dec. 1965, pp. 1007-1009, vol. 58, No. 12.

Wrong, O. M., "Role of the Human Colon in Homeostasis," Scientific Basis of Medicine Annual Reviews, 1971, pp. 192-215.

European Search Report Issued in EP05731099, dated May 8, 2007, 3 pages.

* cited by examiner

METHODS AND COMPOSITIONS FOR TREATMENT OF ION IMBALANCES

CROSS-REFERENCE TO RELATED APPLICATIONS

This application is a divisional of U.S. patent application Ser. No. 11/095,760, filed Mar. 30, 2005, now U.S. Pat. No. 7,776,319, which is a continuation-in-part of U.S. patent application Ser. No. 10/965,274, filed Oct. 13, 2004, now U.S. Pat. No. 7,488,495 issued on Feb. 10, 2009, which is a continuation-in-part application of U.S. patent application Ser. No. 10/814,527, filed Mar. 30, 2004, now U.S. Pat. No. 7,854,924; U.S. patent application Ser. No. 10/814,749, filed Mar. 30, 2004, U.S. Pat. No. 8,192,758; and U.S. patent application Ser. No. 10/813,872, filed Mar. 30, 2004, now U.S. Pat. No. 8,282,960, which are incorporated herein by reference in their entirety.

BACKGROUND OF THE INVENTION

At present, approximately 58 million American adults have hypertension, and its direct and indirect costs are estimated to be more than a quarter of a trillion dollars a year. Hypertension is considered to be the leading factor for stroke and is associated with a high rate of morbidity and mortality when diagnosed in the late stages. Hypertension is a disorder characterized by high blood pressure, i.e., systolic pressure consistently higher than about 140 or diastolic blood pressure consistently over about 90. Many factors affect blood pressure including volume of fluid in the body, salt content of the body, condition of the kidneys, nervous system, or blood vessels, and levels of various hormones in the body. 35% of Caucasian and 65% of African-American hypertension patients are characterized by salt/water retention. Hypertension and diabetes are the most common causes of End Stage Renal Disease (ESRD). The non-pharmacological approach to treating hypertension consists of salt restriction, weight control, and stress management. Control of sodium intake prevents one third of hypertension cases and is a useful adjunct therapy in another third of the cases.

The National Heart, Lung, and Blood Institute (NHLBI) recommends that as part of an overall healthy diet, Americans should consume no more than 2.4 gm (100 mmol) of sodium per day. This equals about 6 grams of sodium chloride. However, the average American diet consists of an estimated 8-12 gm of salt per day. In fact, the recommended salt intake is even lower for patients with late stage renal disease and those at risk of developing hypertension.

Common hypertension treatments include calcium channel blockers, diuretics, beta blockers, alpha blockers, anxiety medication, ACE inhibitors and vasodilators. Recent studies recommend that diuretics be used as the preferred initial stand-alone treatment or as part of a combination treatment for patients suffering from hypertension.

Diuretics are drugs that increase the rate of urine flow by interfering with the sodium and water re-absorption in the nephrons. In general, they increase the rate of sodium excretion from the body. Sodium is the main determinant of the water volume outside of the cells (referred to as extra cellular water). A diuretic that causes sodium to be excreted in the urine decreases the volume of the extra cellular water. The increase in sodium excretion restores salt homeostasis and lower tonicity which ultimately translates into lower blood pressure. As the body regulates intra and extra cellular sodium concentration within a very narrow window, the excretion of salt is usually accompanied by the loss of a proportional amount of water. Diuretics fall into four classes depending on their mode and locus of action:

a. carbonic anhydrase inhibitors such as acetazolamide inhibit the absorption of $NaHCO_3$ and $NaCl$ in the proximal tubule;
b. loop diuretics such as furosemide, acting on the loop of Henle by inhibiting the $Na^+/K^+/2Cl^-$ transporters;
c. thiazide type diuretics which inhibit $Na^+/Cl^-$ cotransporters in the distal tubule;
d. potassium sparing diuretics acting on the collecting duct, they decrease the sodium absorption while sparing $K^+$ (i.e., as opposed to the other three categories that promote loss of potassium).

Diuretics are not always effective therapies as they have undesired side effects. The imbalance in the anions induced by sodium transport modification tends to create complications such as acidosis or alkalosis. One of the limitations of diuretic therapy is "diuretic resistance". One definition of diuretic resistance is the failure to excrete at least 90 mmol of sodium within 72 hrs of a 160 mg oral furosemide dose given twice a day. This effect is caused by one or combination of mechanisms: (i) a change in the pharmacokinetic profile of loop diuretics, (ii) compensation of sodium absorption at distal nephron, and (iii) diminished nephron response. Loop diuretics, such as furosemide, exhibit a blood ceiling concentration where the fractional excretion of sodium is maximal. This ceiling effect has serious implications for patients who hardly respond to sub ceiling concentrations. These patients require continuous infusion of the drug to achieve the desired sodium excretion level. Despite several attempts to improve the drug profile or its bioavailability the results of these therapies remain less than would be desired.

Diuretic resistance is thought to happen in one out of three patients with congestive heart failure (CHF). As patients prescribed with a diuretic must adhere to a low sodium diet, another cause of failure of diuretic therapy is the inability of patients to comply with such a low salt diet.

Edema refers to the accumulation of abnormally large fluid volumes in the intercellular space of the body as a result of excessive sodium retention. Edema may be associated with renal insufficiency, nephritic syndrome, nephrotic syndrome, cardiac insufficiency, or hepatic failure. When the mechanisms regulating sodium balance in the body are disrupted, the accumulation of sodium leads to a compensatory accumulation of fluid (to rectify the osmotic imbalance) and observable edema. In patients with functioning kidneys, edema can be treated by limiting sodium intake and by the use of diuretics, which cause the body to excrete more water in the urine (Brater, D. C. (1992) "Clinical pharmacology of loop diuretics in health and disease." Eur Heart J 13 Suppl G: 10-4 and Brater, D. C. (1993) "Resistance to diuretics: mechanisms and clinical implications." Adv Nephrol Necker Hosp 22: 349-69). Diuretics are ineffective in patients who have reduced renal functions and also certain patient populations are non-responsive to diuretics (Brater, D. C. (1981) "Resistance to diuretics: emphasis on a pharmacological perspective." *Drugs* 22(6): 477-94 and Brater, D. C. (1985) "Resistance to loop diuretics. Why it happens and what to do about it." *Drugs* 30(5): 427-43).

Several studies have demonstrated that scavenging of intestinal sodium is possible. However, the amount of resin required for this purpose (in general from 60-100 g/day) is considered unacceptably high for modern therapy. The large doses reflect the low in vitro and lower in vivo binding capacity of these resins. Even in the presence of high sodium diets, sulfonic resins do not remove more than 1 mEq $Na^+$/gm, carboxylic resins not more than 2 mEq $Na^+$/gm and phosphonic resins not more than 0.8 mEq Na$^+$/g (Fourman, P. (1953) "Capacity of a cationic exchange resin (zeo-karb 225) in vivo." *Br Med J* 1(4809): 544-6; Heming, A. E. and T. L. Flanagan (1953) "Considerations in the selection of cation exchange resins for therapeutic use." *Ann N Y Acad Sci* 57(3): 239-51; and McChesney, E. W., F. C. Nachod, et al. (1953) "Some aspects of cation exchange resins as therapeutic agents for sodium removal." *Ann N Y Acad Sci* 57(3): 252-9). Typically, the resins retained only around 25% or less of their in vitro sodium binding capacity when used clinically in patients. These resins were not well-tolerated by the patients because of their gritty or chalky texture and because of their tendency to cause constipation (Heming, A. E. and T. L. Flanagan (1953) "Considerations in the selection of cation exchange resins for therapeutic use." *Ann N Y Acad Sci* 57(3): 239-51).

Thus, it would be beneficial to develop polymeric compositions which remove salt and/or water from the gastrointestinal tract efficiently.

In addition to hypertension patients, patients suffering from end stage renal disease, renal insufficiency, chronic diarrhea, incontinence, congestive heart failure, hepatic cirrhosis, idiopathic edema, and other conditions can benefit from binding of intestinal Na$^+$ and/or water.

Overall, the current treatments for lowering salt and/or water levels in the body are sub-optimal. Hence, there is a need to develop selective, high capacity salt and/or water removal therapies, with fewer side effects for patients.

BRIEF SUMMARY OF THE INVENTION

The present invention provides methods for removing sodium from the gastrointestinal tract of an animal. In some embodiments, the methods generally involve the administration of an effective amount of a sodium-binding polymer. Preferably the sodium-binding polymers have an in vivo sodium-binding capacity in a human of 4 mmol or more per gm of polymer. In other embodiments, the methods involve the administration of core-shell compositions for the removal of sodium from the gastro-intestinal tract. The methods and compositions described herein are useful in the treatment of disorders in which the removal of sodium and/or water from the body of a human is desirable. Diseases that can be treated with the methods and compositions described herein include, but are not limited to, hypertension, chronic heart failure, end stage renal disease, liver cirrhosis, chronic renal insufficiency, fluid overload, or sodium overload.

DETAILED DESCRIPTION OF THE INVENTION

Sodium-Binding Polymeric Compositions

The present invention provides methods, pharmaceutical compositions, and kits for the treatment of animal subjects. The terms "animal subject" and "animal" as used herein includes humans as well as other mammals. In particular, the present invention provides polymeric compositions for the removal of sodium ions. Preferably, these compositions are used for the removal of sodium ions from the gastrointestinal tract of animal subjects.

One aspect of the invention is a method of removing sodium ions with a sodium-binding polymeric composition. In one embodiment, the sodium-binding polymeric composition has high capacity and/or selectivity for binding sodium and does not significantly release the bound sodium in the gastrointestinal tract. Preferably, the sodium-binding polymeric composition does not release the bound sodium in the colon. Even more preferably, the sodium-binding polymeric composition does not introduce detrimental ions. It is preferred that the polymeric composition exhibit selective binding for sodium ions. In one embodiment, due to the selective binding of sodium by the sodium-binding polymeric composition, the composition does not deplete potassium from the body.

It is preferred that the polymeric compositions of the present invention exhibit high capacity and/or selectivity for sodium. The term "high capacity" as used herein encompasses in vivo binding of 4 mmol or more of sodium per gm of polymer. Typically, this in vivo binding capacity is determined in a human. Techniques for determining in vivo sodium binding capacity in a human are well known in the art. For example, following administration of a sodium-binding polymer to a patient, the amount of sodium in the feces can be used to calculate the in vivo sodium binding capacity. Typically, the in vivo sodium binding capacity is determined in a human with no deficiency of a hormone that controls salt excretion, e.g., aldosterones.

In some embodiments, the in vivo sodium binding capacity can be equal to or more than 4 mmol per gm of polymer in a human. Preferably the in vivo sodium binding capacity in a human is about 5 mmol or more per gm, more preferred is about 6 mmol or more per gm, even more preferred is about 7 mmol or more per gm, and most preferred is about 8 mmol or more per gm. In a preferred embodiment, the in vivo sodium binding capacity in a human is about 8 mmol to about 15 mmol per gm in a human.

The capacity of the sodium binding polymers can also be determined in vitro. It is preferred that the in vitro sodium binding capacity is determined in conditions that mimic the physiological conditions of the gastro-intestinal tract. In some embodiments, the in vitro sodium binding capacity is determined in solutions with a pH of about 7.5 or less. In various embodiments, in vitro sodium binding capacity in a pH of about 7.5 or less is equal to or more than 6 mmol per gm of polymer. A preferred range of in vitro sodium binding capacity in a ph of about 7.5 or less is about 6 mmol to about 15 mmol per gm of polymer. Preferably the in vitro sodium binding capacity in a pH of about 7.5 or less is equal to about 6 mmol or more per gm, more preferred is about 8 mmol or more per gm, even more preferred is about 10 mmol or more per gm, and most preferred is about 15 mmol or more per gm.

The higher capacity of the polymeric composition enables the administration of a lower dose of the composition. Typically the dose of the polymeric composition used to obtain the desired therapeutic and/or prophylactic benefits is about 0.5 gm/day to about 25 gm/day. Most preferred is about 15 gm/day or less. A preferred dose range is about 5 gm/day to about 20 gm/day, more preferred is about 5 gm/day to about 15 gm/day, even more preferred is about 10 gm/day to about 20 gm/day, and most preferred is about 10 gm/day to about 15 gm/day.

The term "detrimental ions" is used herein to refer to ions that are not desired to be released into the body by the compositions described herein during their period of use. Typically, the detrimental ions for a composition depend on the condition being treated, the chemical properties, and/or binding properties of the composition. For example, when hypertension is being treated and the composition is used to remove sodium ions, the detrimental ion would be chloride or OH⁻ as these patients frequently have alkalosis. When renal failure is being treated, examples of detrimental ions are $K^+$ and $Ca^{2+}$.

It is also preferred that the compositions described herein retain a significant amount of the bound sodium. Preferably, the sodium is bound by the polymer in the upper gastro-intestinal tract and not released in the lower gastro-intestinal tract. The term "significant amount" as used herein is not intended to mean that the entire amount of the bound sodium is retained. It is preferred that at least some of the bound sodium is retained, such that a therapeutic and/or prophylactic benefit is obtained. Preferred amounts of bound sodium that are retained range from about 5% to about 100%. It is preferred that the polymeric compositions retain about 25% of the bound sodium, more preferred is about 50%, even more preferred is about 75% and most preferred is retention of 100% of the bound sodium. The period of retention is preferred to be during the time that the composition is being used therapeutically and/or prophylactically. In the embodiment in which the composition is used to bind and remove sodium from the gastro-intestinal tract, the retention period is the time of residence of the composition in the gastro-intestinal tract.

In one embodiment, the sodium-binding polymeric composition exchanges protons for sodium ions in the upper gastrointestinal tract and keeps the bound sodium inside the polymeric composition in the colon, where the sodium concentration is typically much lower in comparison with other cations. The latter are typically $K^+$, $Mg^{++}$, $Ca^{++}$, $NH_4^+$, $H^+$ and protonated amines derived from enzymatic amino-acid deamination, and referred to herein as "competing cations."

In another embodiment, the sodium-binding polymeric composition is characterized by a high rate of binding to sodium ions (vs. competing cations), even in an environment wherein the sodium:competing cations ratio is as low as 1:4, such as in the colon.

In yet another embodiment, the sodium-binding polymeric composition is characterized by a high, but non-specific binding of sodium in the upper tract, coupled to a decrease in ion permeability of the resin triggered by a change in the physiological conditions of the gastrointestinal tract. This change in permeability may be effected by pH change from stomach to duodenum or pH change from ileum to colon. In another embodiment, the permeability change can be effected by the presence of secretion (such as bile acids) or metabolites (such as fatty acids) or localized enzymatic activity.

In one embodiment, the sodium-binding polymeric composition comprises of acid type resin, preferably loaded with $H^+$ or $NH_4^+$, and possibly $K^+$. Typically, the $H^+$, $NH_4^+$ are displaced in the upper tract by mostly $Na^+$ and the permeability of the resin to ions is lowered as the resin travels from the upper gastrointestinal tract to the lower gastrointestinal tract. Typically, this change in permeability is modulated by physiological changes in the environment of the various gastrointestinal segments.

In another embodiment, the sodium-binding polymeric composition comprises of sulfonate or phosphonic polymers.

Sodium-Binding Core-Shell Compositions

In one aspect of the invention, a core-shell composition is used for the removal of sodium. Typically in the core-shell compositions, the core comprises of a polymer with a high binding capacity for sodium. The various sodium-binding polymeric compositions described herein can be used as the core component of the core-shell compositions. In some embodiments, the shell modulates the entry of competing solutes across the shell to the core component. In one embodiment, the permeability of the membrane to bound sodium is diminished as the core-shell composition moves through the gastro-intestinal tract. Typically this permeability change is brought about by increased hydrophobicity and/or deswelling of the shell. It is preferred that the shell of the core-shell composition is essentially not disintegrated during the period of residence and passage through the gastro-intestinal tract.

The term "competing solute" as used herein means solutes that compete with sodium for binding to a core component, but that are not desired to be contacted and/or bound to the core component. Typically, the competing solute for a core-shell composition depends on the binding characteristics of the core and/or the permeability characteristics of the shell component. A competing solute can be prevented from contacting and/or binding to a core-shell particle due to the preferential binding characteristics of the core component and/or the decreased permeability of the shell component for the competing solute from the external environment. Typically, the competing solute has a lower permeability from the external environment across the shell compared to that of sodium ions. Examples of competing solutes include, but are not limited to, $K^+$, $Mg^{++}$, $Ca^{++}$, $NH_4^+$, $H^+$ and protonated amines.

In a preferred embodiment, the core-shell composition binds sodium throughout the gastrointestinal tract but prevents the release of sodium in the colon. These properties of the core-shell are modulated by the shell being permeable to sodium in the upper parts of the gastrointestinal tract and being less permeable to sodium in lower gastro-intestinal tract, like the proximal colon. This modulation of the permeability of the shell across the gastro-intestinal tract is referred to herein as the "permeability trap."

In some embodiments, the shell is permeable to both mono- and di-valent cations. In some of the embodiments in which the shell is permeable to both mono- and di-valent cations, the core binds only mono-valent cations, preferably sodium, due to the binding characteristics of the core. In other embodiments, the shell exhibits preferred permeability to sodium ions.

It is particularly preferred that the core-shell compositions and the sodium binding polymeric compositions described herein bind sodium in the parts of the gastro-intestinal tract which have a relatively high concentration of sodium, like about 70 mM to about 140 mM. This bound sodium is then preferred to remain bound to the compositions and not be released in portions of the gastro-intestinal tract with relatively lower concentrations of sodium, like about 10 mM to about 40 mM.

In one embodiment, the shell material protects the core component from the external GI environment. The shell material in some embodiments protects the acid groups of the core polymer and prevents their exposure to the GI environment. In one embodiment, the core component is protected with a shell component comprising of an enteric coating. Suitable examples of enteric coatings are described in the art. For example, see Remington: The Science and Practice of Pharmacy by A. R. Gennaro (Editor), 20$^{th}$ Edition, 2000.

In another embodiment the shell material is engineered to respond to physiological changes in the gastro-intestinal tract so that the shell's permeability is altered. The permeability of the shell is decreased so that hydrophilic ions are no longer able to cross the shell membrane after these ions are bound to the core. Preferably, this decreased permeability is during the period of use of the polymeric composition, i.e., during the period the polymeric composition is resident in the gastro-intestinal tract. The loss of permeability to hydrophilic ions can be accomplished by decreasing or even eliminating the free volume of permeation of the membrane. Since the latter is mostly controlled by the hydration rate of the shell, it is possible to almost shut down the rate of permeation by inducing a shell collapse. Many techniques of inducing such a phase change are known in the art. The preferred approach consists of rendering the membrane material increasingly hydrophobic so that the hydration rate decreases almost to zero. This can be accomplished through several ways depending upon the type of triggering mechanism.

For example the phase change can be triggered by pH change. The pH profile of the gastrointestinal tract may change as a function of time, but show some invariants as indicated below in TABLE 1 (Fallinborg et al. *Aliment. Pharm. Therap.* (1989), 3, 605-613):

TABLE 1

| GI tract segment | pH range |
| --- | --- |
| Stomach | 1-2 |
| Duodenum - distal small intestine | 6-7 |
| Ceacum-ascending colon | 7-5.5 |
| Transverse-descending colon | 5.5-6 |
| Feaces | 6.5 |

Shell polymers exhibiting a chain collapse in any of these pH regions can be used to cause permeability changes. One embodiment of core-shell particles binds sodium ions selectively in the stomach and keeps it in the particle core while the particles are moving down the small and large intestine and display a high permeability to sodium ions at low pH and very low permeability at neutral pH. This can be achieved by having a shell polymer with hydrophobic groups and groups that ionize subject to pH change. For example, polymers built from hydrophobic monomers (e.g. long chain alcohol (meth) acrylates, N-alkyl (meth)acrylamide, aromatic monomers), and basic monomers that ionize at low pH and remain neutral beyond their pKa (e.g. vinyl-pyridine, dialkylaminoethyl (meth)acrylamide). The relationship between pH and shell swelling ratio, and hence permeability, is controlled by the balance of hydrophobic monomers and ionizable monomers. Examples of such systems are reported in the literature (Batich et al, *Macromolecules,* 26, 4675-4680. In one embodiment, the shell of a core-shell composition is characterized by a high permeability for sodium at low pHs such as pH of about 1 to about 5. A core-shell with these properties can bind sodium in the stomach and as the composition passes through to the lower gastro-intestinal tract the permeability is shut down, typically at about neutral pH.

In one embodiment, the shell of a core-shell composition is characterized by a high permeability to sodium at about neutral pHs and above. A core-shell with this property can absorb and bind sodium in the upper gastro-intestinal tract from secretions that are mostly rich in sodium (for example about 140 mM of sodium and about 20 mM of potassium) and when the composition enters the cecum, where the pH range is about 5 to about 6, the shell collapses and reduces its permeability to competing cations. Shell material switches from a hydrated state to a collapsed-impermeable state as the pH gets slightly acidic. In this particular instance, shell polymers typically contain a balanced amount of hydrophobic and acidic monomers. Systems that can be used in the shell of this embodiment are described in the literature. For example, see Kraft et al. *Langmuir,* 2003, 19, 910-915; Ito et al, *Macromolecule,* (1992), 25, 7313-7316.

In another embodiment, the shell of a core-shell composition displays a permeability change by passive absorption while passing through the upper GI tract. Many components present in the GI tract including components of the diet, metabolites, secretion, etc. are susceptible to adsorb on and within the shell in a quasi-irreversible manner and strongly modify the permeability pattern of the shell. The vast majority of these soluble materials are negatively charged and show various levels of hydrophobicity. Some of those species show a typical amphiphilic character, such as fatty acids, phospholipids, bile salts and behave as surfactants. Surfactants can adsorb non-specifically to surfaces through hydrophobic interactions, ionic interaction and combinations thereof. In this embodiment, this phenomenon is used to change the permeability of the polymeric composition upon the course of binding sodium ions. In one embodiment fatty acids can be used to modify the permeability of the shell and in another embodiment bile acids can be used. Fatty acids and bile acids both form aggregates (micelles or vesicles) and can also form insoluble complexes when mixed with positively charged polymers (see e.g. Kaneko et al, *Macromolecular Rapid Communications* (2003), 24(13), 789-792). Both fatty acids and bile acids exhibit similarities with synthetic anionic surfactants and numerous studies report the formation of insoluble complexes between anionic surfactants and cationically charged polymers (e.g. Chen, L. et al, *Macromolecules* (1998), 31(3), 787-794). In this embodiment, the shell material is selected from copolymers containing both hydrophobic and cationic groups, so that the shell forms a tight complex with anionically charged hydrophobes typically found in the GI tract, such as bile acids, fatty acids, bilirubin and related compounds. Suitable compositions also include polymeric materials described as bile acids sequestering agents, such as those reported in U.S. Pat. Nos. 5,607,669; 6,294,163; and 5,374,422; Figuly et al, *Macromolecules,* 1997, 30, 6174-6184. The formation of the complex induces a shell membrane collapse which in turn can lower or even shut down the permeation rate across the membrane. A core-shell with these properties can absorb and bind sodium in the upper gastrointestinal tract, like stomach and duodenum, and as bile acid and fatty acid molecules bind to the shell further down in the gastrointestinal tract the permeability of the shell to ions, including sodium, is decreased as the shell porosity is hindered by the bile acid and/or fatty acid molecules. Further, an interaction between the bile and fatty acids with the shell prevents their interaction with the core and can thus preserve the sodium-binding capacity of the core component.

In yet another embodiment, the permeability of the shell of a core-shell composition is modulated by enzymatic activity in the gastro-intestinal tract. There are a number of secreted enzymes produced by common colonic microflora. For example *Bacteroides, Prevotella, Porphyromonas,* and *Fusobacterium* produce a variety of secreted enzymes including collagenase, neuraminidase, deoxyribonuclease [DNase], heparinase, and proteinases. In this embodiment the shell comprises a hydrophobic backbone with pendant hydrophilic entities that are cleaved off via an enzymatic reaction in the gut. As the enzymatic reaction proceeds, the polymer membrane becomes more and more hydrophobic, and turns from a high swollen state, high permeability rate material to a fully collapsed low hydration membrane with minimal permeability. Hydrophilic entities can be chosen from natural substrates of enzymes commonly secreted in the GI tract. Such entities include amino acids, peptides, carbohydrates, esters, phosphate esters, oxyphosphate monoesters, O- and S-phosphorothioates, phosphoramidates, thiophosphate, azo groups and the like. Examples of enteric enzymes susceptible to chemically alter the shell polymer include, but are not limited to, lipases, phospholipases, carboxylesterase, glycosidases, azoreductases, phosphatases, amidases and proteases. The shell can be permeable to sodium ions until it enters the proximal colon and then the enzymes present in the proximal colon could react chemically with the shell to reduce its permeability to the sodium ions.

In some embodiments, the shell thickness can be between about 0.002 micron to about 50 micron, preferably about 0.005 micron to about 20 microns. Preferably the shell thickness is more than about 1 micron, more preferred is more than about 10 micron, even more preferred is more than about 20 micron, and most preferred is more than about 40 micron. Preferably the shell thickness is less than about 50 micron, more preferred is less than about 40 micron, even more preferred is less than about 20 micron, and most preferred is less than about 10 micron.

The size of the core-shell particles typically range from about 200 nm to about 2 mm, preferably being about 500 μm. Preferably the size of the core-shell particles are more than about 1 μm, more preferred is more than about 100 μm, even more preferred is more than about 200 μm, and most preferred is more than about 400 μm. Preferably the size of the core-shell particles are less than about 500 μm, more preferred is less than about 400 μm, even more preferred is less than about 200 μm, and most preferred is less than about 100 μm.

Sodium-Binding Polymers

In one embodiment, the sodium-binding polymer used in the polymeric compositions and core-shell compositions is a sulfonic ($-SO_3^-$), sulfuric ($-OSO_3^-$), carboxylic ($-CO_2^-$), phosphonic ($-PO_3^-$), phosphoric ($-OPO_3^-$), or sulfamate ($-NHSO_3^-$) type functional polymer. Free radical polymers derived from monomers such as vinyl sulfonate, vinylphosphonate, or vinylsulfamate can also be used. Preferably, the polymers used can bind sodium in a wide range of pH.

Examples of other suitable monomers for sodium-binding polymers are included in Table 2.

TABLE 2

Examples of cation exchange moieties-structures and theoretical binding capacities

| | Molar mass per charge | Theoretical capacity | Fraction of titrable H @pH 3 | Fraction of titrable H @ pH 6 | Expected Capacity @pH3 | Expected Capacity @pH6 |
|---|---|---|---|---|---|---|
|  | 74 | 13.5 | 0.05 | 0.5 | 0.68 | 6.76 |
|  | 92 | 10.9 | 0.2 | 0.95 | 2.17 | 10.33 |
|  | 53 | 18.9 | 0.25 | 0.5 | 4.72 | 9.43 |
|  | 47.5 | 21.1 | 0.25 | 0.5 | 5.26 | 10.53 |
|  | 57 | 17.5 | 0.1 | 0.5 | 1.75 | 8.77 |
|  | 107 | 9.3 | 1 | 1 | 9.35 | 9.35 |
|  | 93 | 10.8 | 1 | 1 | 10.75 | 10.75 |
|  | 63 | 15.9 | 0 | 0.4 | 0 | 6.35 |

TABLE 2-continued

Examples of cation exchange moieties-structures and theoretical binding capacities

| | Molar mass per charge | Theoretical capacity | Fraction of titrable H @pH 3 | Fraction of titrable H @ pH 6 | Expected Capacity @pH3 | Expected Capacity @pH6 |
|---|---|---|---|---|---|---|
|  | 125 | 8 | 1 | 1 | 8 | 8 |
|  | 183 | 5.5 | 1 | 1 | 5.46 | 5.46 |
|  | 211 | 4.7 | 1 | 1 | 4.74 | 4.74 |

Other suitable cation exchange moieties include:

wherein n is equal to or greater than one and Z represents either SO₃H or PO₃H. Preferably n is about 50 or more, more preferably n is about 100 or more, even more preferred is n about 200 or more, and most preferred is n about 500 or more.

Suitable phosphonate monomers include vinyl phosphonate, vinyl 1,1 bis phosphonate, and ethylenic derivatives of phosphonocarboxylate esters, oligo(methylenephosphonates), and hydroxyethane-1,1-diphosphonic acid. Methods of synthesis of these monomers are well known in the art. Sulfamic (i.e. when Z=SO₃H) or phosphoramidic (i.e. when Z=PO₃H) polymers can be obtained from amine polymers or monomer precursors treated with a sulfonating agent such as sulfur trioxide/amine adducts or a phosphonating agent such as P₂O₅, respectively. Typically, the acidic protons of phosphonic groups are exchangeable with cations, like sodium, at pH of about 6 to about 7.

Another example of a suitable monomer for use herein is α-fluoroacrylate. This monomer is typically prepared from chloroacetate ester. See K F Pittman, C. U., M. Ueda, et al. (1980). *Macromolecules* 13(5): 1031-1036. Other methods comprise the step-growth polymerization from phosphonate, carboxylic, phosphate, sulfinate, sulfate and sulfonate functionals compounds. High density polyphosphonates such as those marketed Rhodia under the trademark Briquest are particularly useful.

The polymers of the invention also include ion exchange resins synthesized from naturally occurring polymers, such as saccharide polymers and semi-synthetic polymers, optionally functionalized to create ion exchange sites on the backbone or on the pendant residues. Examples of polysaccharides of interest include materials from vegetal or animal origins, such as cellulosic materials, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin and chitosan. Most preferred are polymers that do not degrade under the physiological conditions of the gastrointestinal tract and remain non-absorbed, such as carboxymethylcellulose, chitosan, and sulfoethylcellulose.

Cation and Anion Binding Polymers

One embodiment of the invention utilizes both an acid resin (for example, sulfonate in the proton form) and a strong base resin (for example, quaternary ammonium in the OH⁻ form) or a weak base resin (for example, a free amine). This composition can release water upon the exchange of H⁺ for Na⁺ and OH⁻ for Cl⁻. In yet another embodiment, the polymer contains an internal salt of an acid and a base function, free of counter ions. In this embodiment, the combination with an anion binding resin has the advantage of increasing excretion of chloride ions from the body (the most dominant anion in the upper GI environment) and therefore minimizes acidosis in kidney compromised patients.

In one embodiment, the polymeric composition that can bind sodium has the ability to swell from about 2 to about 100 times its weight in an isotonic fluid composition. The polymer in one embodiment is an acid stable fluid absorbing polymer that can take up about 10-about 50 times its weight in saline solution and have the ability to retain this absorbed fluid under pressure, for example, under pressure that occurs upon volume reduction in the human colon. Based on the polymer structure the fluid uptake can be pH dependent and the uptake of saline solution can be prevented in the stomach and occur in the gastrointestinal tract. The site of fluid uptake can be modified based on the polymer structure, including by crosslinking, counterions, molecular weight, charge density, crosslinking density or coatings.

In one embodiment, the invention utilizes a cation exchange resin in the acidic form and an anion exchange resin in the basic form, i.e. the positively charged anion exchange site on the polymer is compensated by OH⁻. Alternatively, the polymer can be a free base that protonates upon contact with the aqueous gastrointestinal fluid. The resins can be independently water-soluble or crosslinked materials; preferably both resins are crosslinked. The anion (OH⁻) exchange to cation (H⁺) exchange mole ratio is preferably about 0.5 to about 1.5, most preferably about 0.9 to about 1.1.

The ion exchange resins can be obtained by free radical polymerization, by copolymerization of functional monomers, polymer post-functionalization or combinations thereof. Examples of cation exchange groups are those listed in table 2. Examples of anion exchange groups are: amine (—NR$_3$), quaternary ammonium (—NR$_4^+$), amidine (—C(=NH)—NH$_2$), guanidine (—NH—C(=NH)—NH$_2$), phosphonium (—PR$_3^+$).

Methods of preparation of the polymers with ion exchange resins are well known to a person skilled in the art. For example, see Ion Exchange, Charles Dickert, Kirk-Othmer Encyclopedia of Chemical Technology, © 1995 by John Wiley & Sons, Inc. Ion exchange resins can be prepared by a variety of processes including bulk, solution, emulsion, suspension, dispersion, precipitation, or with the use of water or organic solvents. When necessary, process auxiliaries are used, including free radical initiators, redox initiating systems, crosslinking agents, branching agents, chain transfer agents, suspending agents, wetting agents, stabilizers, porogen, diluents, light and heat stabilizers, and plasticizers. The polymer can be shaped in the form of, for example, a powder, bead, sheet, fiber, capsule, or membrane.

It is preferred that the ion exchange capacities of the polymers described herein are maximal to retain the highest load of salt (e.g. expressed as NaCl). The higher the capacity, the lower the dose of polymer required to excrete a given quantity of salt. The capacity can be expressed as mEq of exchangeable ion per gram of polymer. The weight of sodium chloride absorbed by one gram of polymer as a function of the polymer capacity can be computed as follows:

$$W_{Nacl} = 58.44 \cdot 10^{-3}/(C_{an}^{-1} + C_{cat}^{-1}),$$

where $C_{an}$ is the capacity of the anion exchange resin, and $C_{cat}$ is the capacity of the cation exchange resin. In preferred embodiments of the present invention, $W_{Nacl}$ ranges from about 0.05 to about 1, preferably about 0.2 to about 0.7, most preferably about 0.3 to about 0.5. $C_{an}$ and $C_{cat}$ are preferably between about 2 to about 30 mEq/gr, preferably from about 5 to about 25 mEq/gr, most preferably between about 10 and about 20 mEg/gr.

Examples of suitable anion exchange polymers are:

In these structures, N represents a nitrogen atom linked to substituents in order to respect nitrogen valency: examples of substituents are listed hereafter (but not limited to): —NR$_2$, —N$^+$R$_3$, —NR—CH=NR, —NR—C(=NR)NR$_2$, with R being H, alkyl, aryl, acyl, optionally substituted.

The anion exchange resins can also be synthesized from naturally occurring polymers, such as saccharide polymers and semi-synthetic polymers, optionally functionalized to introduce amine functionality on the backbone or on the pendant residues. They can be prepared by nucleophilic substitution reactions under alkaline conditions. A Michael addition can be used to prepare cyanoethylated cellulose or carbamoyl cellulose by treating cellulose with acrylonitrile or acrylamide, respectively. The preparation of primary aminoalkyl cellulosics generally involves reacting activated cellulose with aminoalkyl halides, aminoalkylsulfuric acid, or ethylenimine. Another method to prepare aminoalkyl cellulosics involves the direct reduction of the nitrile group of cyanoethylated cellulose to give aminopropyl cellulose. The Hofmann rearrangement of carbamoylethylcellulose with bromine/NaOH for 30-120 min also gives aminopropyl cellulose. Reacting activated cellulose with epichlorohydrin, followed by subsequent reaction with various diamines gives O-[2-Hydroxy-3-(ω-aminoalkylamino) propyl cellulose. A water soluble 2-aminoethyl-carbamoyl cellulose with a low degree substitution (DS<0.02) may be prepared by treating sodium carboxymethyl cellulose with excess ethylenediamine in the presence of water soluble carbodiimides.

In one embodiment, the basic and acidic resins are enclosed in a compartment isolated from the gastrointestinal fluid by an ion-permeable membrane. Use of a membrane to surround the resins that are in close proximity reduces the pH variation following the uptake of salt. For instance the two types of resins can be encased in a dialysis bag, paper bag, microporous matrix, polymer gel, hollow fibers, vesicles, capsules, tablet, or a film.

Figure 1:
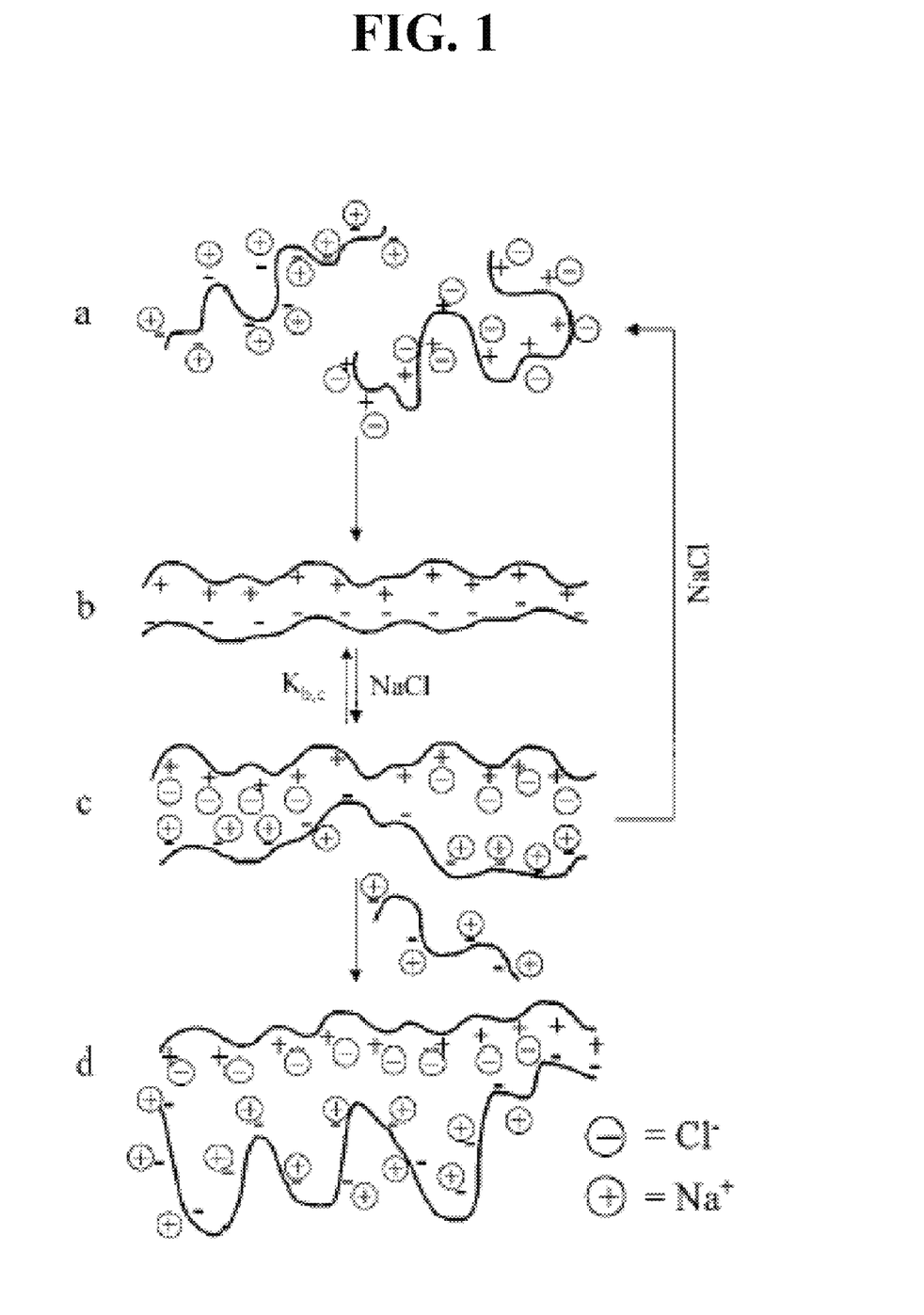
FIG. 1 is a schematic representation of the formation of a polyelectrolyte complex.

In one embodiment, the salt removal polymer comprises an internal salt of a polyelectrolyte complex prepared from polymers of opposite charges, the polymer being capable of removing ions from the gastrointestinal tract and not introducing detrimental ions. This material is referred to herein as polyelectrolyte complex (PEC). The formation of a complex is schematically represented in FIG. 1. One polycation and one polyanion are mixed in a stoechiometric ratio until an insoluble complex precipitates.

The PEC forms as a result of cooperative electrostatic interaction between the polymers of opposite charges and from a gain of entropy produced by the release of the small molecule counter-ions. Further washing or dialysis leads to a salt free material: almost all the charges on the polymers are internally compensated. When this material is contacted with an aqueous solution of a finite salt concentration, and if the salt concentration is high enough, then the coulombic interaction between polycation and polyanion is screened by the electrical field produced by the added electrolyte, and the complex becomes soluble. In this situation each charge on both polymers is compensated by a counter ion coming from the surrounding solution. The net result is an uptake of salt by the polymer from the aqueous solution through an ion-exchange process. When the PEC is fully solubilized the quantity of salt retained by the polymer equals the mole content of internal salt initially present in the polymer complex.

In one embodiment, a complex is first formed by adding the two polymers at the required mole ratio to form a complex precipitate, which is subsequently washed from the released salt. When the salt free polymer complex is taken orally, upon contact with the gastrointestinal content, the physiological ionic strength is sufficient to nullify the coulombic interaction within the PEC, so that each charged polymer strand becomes soluble while scavenging one equivalent of salt (mainly NaCl). The polyelectrolytes remain soluble in the gastrointestinal tract and prevent their associated counter-ions to be reabsorbed, until excretion in the feces.

The preparation and physical chemistry of PECs is well known in the art. For example, see A. S Michael et al. J. Phys. Chem. 65, 1765 (1961); J. Phys. Chem. 69, 1447 (1965); J. Phys. Chem. 69, 1456 (1965); J. Phys. Chem. 65, 1765 (1961); Bixler et al., Encycl. Polym. Sci. Tech. 10, 765 (1969); Kabanov et al., Chem. Reviews, 4, 207-283 (1982); Tsuchida et al., J. Polym. Sci. Polym. Chem. Ed., 10, 3397 (1972). PEC's are widely used in the art in microencapsulation of drugs, enzymes, cells, microorganisms, Langerhans islets, polyelectrolytes multilayers as sensors, immobilization of proteins by complex formation, and polycation complexes with DNA as vectors in gene therapy. In these prior art applications, the PEC's retain a solid gel structure at physiological salt concentrations. However, the PEC's of the present invention undergo salt-induced resolubilization at physiological salt concentrations which then enables the polymer to remove salts from the physiological fluid in the gastrointestinal tract.

It is preferred that the PEC's and the polymers constituting the PEC's fulfill one or more conditions to provide salt removing properties under conditions prevailing in the gastrointestinal tract: the polymers and their complex are non absorbable, non irritable, non-toxic, and non-inflammatory. It is also preferred that the polymers, once freed from the complex, should not produce high osmotic pressure so that no significant undesirable intestinal events occur, such as bowel movement and osmotic diarrhea. The solubilization of the PEC can be triggered at an electrolyte concentration typical of the intestinal tract. The solubilization of the PEC can occur at about 50-200 mM expressed in NaCl, usually about 100 mM. It is further preferred that the polymer, either as a gel or as aqueous solution, not change adversely the consistence of the stool or provoke constipation.

The PEC's of the present invention with salt removing properties fall into 3 categories in some embodiments: (i) both polymers are soluble and distinct from each other; (ii) one polymer is a crosslinked gel while the other polymer is soluble, the crosslinked material preferably being the cationic component; or (iii) both polymers are co-crosslinked in a gel material. The PEC in which both polymers are co-crosslinked in a gel material, a transition from a collapsed state to a swollen state occurs in the presence of salt, wherein the collapsed gel (internal salt) starts absorbing the surrounding salt, including NaCl.

Typically, each PEC has a salt concentration beyond which the complex falls apart, i.e., solubilizes or swells. This is one of the characteristics of the PEC that controls the required salt removal property in the gastrointestinal environment. The solubilizing salt concentration (or the gel swelling salt concentration when one deals with a crosslinked gel) depends on a number of factors such as the charge density on both polymers, the geometrical constraints to form an internal salt (charge density match between the anionic and cationic components), the molecular weights, the overall hydrophocity of the polymer backbones, and the mole ratio between cationic and anionic sites.

The polymers of the present invention can be hydrophilic polymers with moderate charge densities, a mismatch in charge densities between cations and anions, and non-stoichiometric ratios displaying salt solubilizing properties at salt concentrations in the desired physiological ranges. The preferred ranges of charge densities (expressed as anion or cation capacity in mEq/gr) are about 5 mEq/gr to about 25 mEq/gr, most preferred 5 mEq/gr to 10 mEq/gr. A preferred charge density mismatch (measured as the ratio of anion capacity to cation capacity: a ratio departing from 1 translates into a density mismatch) is about 0.2 to about 0.8 and about 1.2 to about 1.8, most preferred being about 0.5 to about 0.8 and about 1.2 to about 1.5. A preferred stoichiometric ratio of cation/anion is about 1.00+/−0.01 to about 1.00+/−0.5, most preferred being about 1.00+/−0.05 to about 1.00+/−0.3.

The polymers of the present invention can be homopolymers or copolymers, wherein the ionic monomer molar fraction can range from about 0.10 to about 1. Other polymer architectures such as block, star and graft, and gradient copolymers can also be advantageous. Block copolymers are known to assemble into micelles, these micelles can be crosslinked in the core or in the shell domain. Such segmented architectures can be produced through living free radical polymerization methods such as RAFT or ATRP. When soluble polymers are used, the molecular weight is preferably between about 5000 gm/mole to about 5,000,000 gm/mole, preferably about 50,000 gm/mole to 1,000,000 gm/mole. When star and micellar-type polymers are used, molecular weights are typically comprised between 50,000 to 100,000,000 gm/mole. Finally when the polymers are crosslinked, the molecular weight is by definition infinite. Crosslinked polymers, used according to the various embodiments of the invention, can adopt several formats, including beads with diameters ranging from about 10 nanometers to several hundreds of microns.

Synthesis of Core-Shell Compositions

Examples of processes that can be used to synthesis suitable core-shell compositions are the inverse suspension process and direct suspension process.

In the inverse suspension process, the hydrophilic core can be produced by inverse free radical polymerization using a block copolymer as the surfactant. Suitable monomers include vinylsulfonate, maleic acid, vinyl-phosphonate, vinyl-bis-phosphonate, acrylic acid, α-fluoro acrylic acid, styrene sulfonate, and acrylamido-methyl-propane sulfonic acid (AMPS), or their salts. The shell can be produced by a block copolymer with one block comprising the shell material (e.g. cationic and hydrophobic) and the other block being soluble and co-reactive with the core polymer.

Further techniques for the synthesis of core-shell compositions are described in co-pending patent application entitled, "Ion Binding Compositions,"filed on Mar. 30, 2004, application Ser. No. 10/814,749.

One useful process consists of converting sulfonic monomers to their ester forms, which then become much less water soluble and therefore amenable to direct mini-emulsion polymerization. The shell can be produced by a second stage monomer addition to encapsulate the core. The final material is hydrolyzed in acidic conditions.

In one embodiment, the shell material is designed to interact with bile acids and/or fatty acids, preferably in an irreversible manner. Suitable bile acid binders that can be used in the shell include Cholestyramine, Welchol, and the suitable compositions disclosed in U.S. Pat. No. 5,633,344, Macromolecules, 1997, 30, 6174-84 and J. Pharma Sci. 86, 1, 1997. One example of a suitable monomer that can be used in the shell is 11-trimethylammoniounddecylmethacrylate.

Another useful process comprises of first forming an amine functional polymer such as polyallylamine, polyvinylamine or polyethylenimine, and next treating with a sulfonating agent such as $SO_3$/trimethylamine, or alternatively a phosphonating agent such as $P_2O_5$. Other polymer precursors can also be used, e.g. polystyrene, polybutadiene, polyisoprene, polypropylene, EPDM rubber and the like.

In another process, highly sulfonated or highly phosphonated polymers are obtained from amine functional polymers, which are then post-reacted with vinylsulfonic, vinyl phosphonic or vinyl diphosphonic acid through Michael additions.

Treatment of Ion Imbalances and Fluid Overload

The present invention includes methods of treatment using the polymers described above. The sodium binding polymeric compositions and sodium-binding core-shell compositions described herein can be used to treat diseases wherein a reduction in physiological levels of salt and/or water are desired. The patient populations that the compositions and methods described herein are particularly useful in include, but are not limited to, congestive heart failure, hypertension, diabetes, chronic renal insufficiency, end stage renal disease, and liver cirrhosis. Also, suitable patient populations include patients suffering from fluid overload and/or salt overload. Another suitable patient population includes patients who are resistant to diuretic therapy and are suffering from hypertension, chronic heart failure, end stage renal disease, liver cirrhosis, chronic renal insufficiency, fluid overload, or a combination thereof. The compositions described herein are also useful in the treatment of peripheral edema, including premenstrual and mixed-type edema, and edema of pregnancy with or without hypertension, including pre-eclampsia.

In one embodiment, the patients treated with the compositions described herein benefit from the removal of small amounts of salt constantly over an extended period of time. In another embodiment, the patients benefit from the removal of extra-cellular water and thus have a beneficial effect on fluid management, blood pressure control, interdialytic weight gain and other aspects commonly related to fluid overload when suffering from hypertension, chronic heart failure, end stage renal disease, liver cirrhosis, and/or chronic renal insufficiency. In yet another embodiment, in patients suffering from end stage renal disease and chronic renal insufficiency, the removal of both sodium and chloride helps address acidosis. The use of the compositions described herein can prevent formation of edema after a cardiac event in a patient. Also, the compositions are suitable for treatment of patients suffering from volume/salt sensitive diastolic heart failure.

In end stage renal disease patients, the compositions of the present invention cause the removal of sodium and thus can cause a reduction in fluid overload. The removal of sodium helps to keep the blood volume under control to treat hypertension. Treatment with the compositions of the present invention can enable a reduction in the dosing and/or replace current hypertension treatments such as calcium channel blockers and minimize water weight gains between dialysis sessions that can have a significant impact on the heart, duration of dialysis and overall quality of life.

The polymers of the present invention are also useful in the treatment of patients with diabetic and hypertensive nephropathy. Typically, these patients develop resistance to diuretic therapy due to the reduced kidney function. In this patient population the polymers of the present invention causes removal of sodium which in turn allows to reduce hypertension and preserve kidney function. The polymers may be used alone or in combination with vasodilators.

The present compositions can also be used to treat hypertension patients. Other patients that can benefit from treatment with the compositions of the present invention include patients suffering from chronic heart failure, diarrhea, incontinence, and liver cirrhosis patients.

The term "treating" and its grammatical equivalents as used herein include achieving a therapeutic benefit and/or a prophylactic benefit. By therapeutic benefit is meant eradication or amelioration of the underlying disorder being treated. For example, in a hypertension patient, therapeutic benefit includes eradication or amelioration of the underlying hypertension. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For example, administration of a polymer of the present invention to a patient suffering from hypertension provides therapeutic benefit not only when the patient's blood pressure is decreased, but also when an improvement is observed in the patient with respect to other symptoms that accompany hypertension like headaches. For prophylactic benefit, a polymer may be administered to a patient at risk of developing hypertension or to a patient reporting one or more of the physiological symptoms of hypertension, even though a diagnosis of hypertension may not have been made.

The present invention also includes kits comprising the compositions described herein. These kits comprise of at least one of the compositions of the present invention and instructions teaching the use of the kit according to the various methods described herein.

Combination Therapies

In all the suitable patient populations the polymeric compositions of the present invention can be co-administered with other treatments. For example, the compositions can be administered with other standard hypertension and congestive heart failure treatments. In hypertension patients, the polymers can be co-administered with standard hypertension therapy including, but not limited to, calcium channel blockers, diuretics, beta blockers, alpha blockers, anxiety medication, ACE inhibitors, vasodilators, and angiotensin II receptor blockers. By "co-administration" it is intended to mean herein simultaneous administration of the therapeutic agents in the same dosage form, simultaneous administration in separate dosage forms, and separate administration of the therapeutic agents. For example, a polymer of the present invention can be simultaneously administered with a diuretic, wherein both the polymer and diuretic are formulated together in the same tablet. Alternatively, the polymer could be simultaneously administered with the diuretic, wherein both the polymer and diuretic are present in two separate tablets. In another alternative, the polymer could be administered first followed by the administration of the diuretic, or vice versa. In one embodiment, the compositions described herein are co-administered with a laxative.

Formulations and Routes of Administration

The polymeric compositions and core-shell compositions described herein or pharmaceutically acceptable salts thereof, can be delivered to the patient using a wide variety of routes or modes of administration. The most preferred routes for administration are oral or intestinal.

The term "pharmaceutically acceptable salt" means those salts which retain the biological effectiveness and properties of the polymers used in the present invention, and which are not biologically or otherwise undesirable. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the polymers used in the present invention contain a carboxy group or other acidic group, it may be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine and triethanolamine.

If necessary, the polymers and core-shell compositions may be administered in combination with other therapeutic agents. The choice of therapeutic agents that can be co-administered with the compounds of the invention will depend, in part, on the condition being treated.

The polymers (or pharmaceutically acceptable salts thereof) may be administered per se or in the form of a pharmaceutical composition wherein the active compound(s) is in admixture or mixture with one or more pharmaceutically acceptable carriers, excipients or diluents. Pharmaceutical compositions for use in accordance with the present invention may be formulated in conventional manner using one or more physiologically acceptable carriers compromising excipients and auxiliaries which facilitate processing of the active compounds into preparations which can be used pharmaceutically. Proper formulation is dependent upon the route of administration chosen.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions, wafers, and the like, for oral ingestion by a patient to be treated. In one embodiment, the oral formulation does not have an enteric coating. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For administration orally, the compounds may be formulated as a sustained release preparation. Numerous techniques for formulating sustained release preparations are known in the art.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for administration.

Effective Dosages

Pharmaceutical compositions suitable for use in the present invention include compositions wherein the sodium-binding polymers are present in an effective amount, i.e., in an amount effective to achieve therapeutic and/or prophylactic benefit. The actual amount effective for a particular application will depend on the condition being treated and the route of administration. Determination of an effective amount is well within the capabilities of those skilled in the art, especially in light of the disclosure herein.

The effective amount for use in humans can be determined from animal models. For example, a dose for humans can be formulated to achieve gastrointestinal concentrations that have been found to be effective in animals.

A skilled person using techniques known in the art can determine the effective amount of the polymer. In one embodiment, an effective amount of sodium-binding polymer is the amount that will decrease diastolic and/or systolic pressure in a hypertension patient; preferably bring the blood pressure down to a normal range. In some embodiments, the decrease is about 20% to about 40%. The effective amount can also be an amount that increases the fecal excretion of sodium. An increase of sodium excretion of about 10 to about 150 mmol per day is preferred, an increase of about 20 mmol to about 100 mmol per day is even more preferred; and most preferred is an increase of about 40 mmol to about 80 mmol per day.

EXAMPLES

Example 1

Measurement of Sodium Binding Capacity In Vitro

The resin material is treated with 1M HCl and washed repeatedly with water. A weighted aliquot is then titrated with 0.1M NaOH and the capacity recorded as the mole amount of base needed to reach the desired pH (usually 6). Alternatively, the resin is soaked in 1M NaCl solution buffered at the desired pH, washed with water, and finally treated with 0.5M KCl. The sodium released is then titrated by ion-exchange chromatography and the sodium binding capacity calculated accordingly. Polymer beads described in the examples hereafter, typically give a Na binding capacity in the range of about 6 to 10 mmol/gr.

Example 2

Synthesis of Sodium Binding Polymeric Compositions

A. Synthesis of Polyvinylsulfonate Polymer Beads

Vinyl sulfonate monomer is first polymerized in water with sodium persulfate as a free radical initiator in a pressure-proof reactor at 110° C. Polyvinylsulfonate oligomers are isolated by precipitation in acetone. Oligomers are then treated with thionylchloride to form vinylsulfonate-co-vinylsulfonylchloride copolymers. Beads are obtained by dispersing a vinylsulfonate-co-vinylsulfonylchloride oligomer solution in toluene, then adding diamino-propane to form the desired beads. Final beads are washed extensively with water, 1M HCL, and water successively.

B. Synthesis of Polyvinylsulfamate Polymer Beads by Inverse Suspension Polymerization 100 parts of vinylformamide/methylene-bis-acrylamide in a 90/10 weight ratio are solubilized in 100 parts of water with 1 part of sodium persulfate as an initiator; the mixture is then dispersed in 200 parts of toluene and one part of sorbitol sesquioleate as a surfactant, using a high-shear homogenizer. The emulsion is kept under mechanical agitation at 80° C. for 8 hours. The beads are then filtered, washed with acetone, and hydrolyzed in 1M HCl for 6 hours at 50° C. to polyvinylamine crosslinked beads. The beads are then treated with trimethylamine/$SO_3$ to yield the desired polyvinylsulfamate particles.

C. Synthesis of Polyvinylsulfamate/Vinylsulfate Copolymer Beads.

The above process (Example 2B) is repeated except that 30 mol-% of vinylformamide is replaced by vinylacetate.

D. Synthesis of Polyvinylphosphoramidic Polymer Bead

The above process (Example 2B) is repeated except that the polyvinylamine groups are treated with $P_2O_5$.

E. Synthesis of N-(bis-phosphonic-ethyl) Polyvinylamine Beads

The above process (Example 2B) is repeated except that the polyvinylamine groups are further treated with diethylvinylphosphonate, and the resulting polymer hydrolyzed to the phosphonic form.

F. Synthesis of poly-α-fluoroacrylic Acid Beads

First α-fluoroacrylic acid is prepared from chloroacetate ester and KF, following procedure described in Pittman, C. U., M. Ueda, et al. (1980). *Macromolecules* 13(5): 1031-1036. Beads are prepared by a direct suspension process where a mixture of α-fluoroacrylic methyl ester/divinylbenzene/benzoyl peroxide in a weight ratio 90/9/1 are dispersed in water under high shear with hydroethylcellulose as a suspending agent. The suspension is stirred and heated at 80° C. for 10 hours. The residual monomer is eliminated by steam stripping. The beads are then filtered and treated with HCl to hydrolyze the polymer to form the desired polyα-fluoroacrylic acid particles.

G. (Polyα-fluoroacrylic Acid) Core/(Poly-11 trimethylammonioundecylmethacrylate) Shell Particle Crosslinked α-fluoroacrylic methyl ester polymer particles are prepared by mini-emulsion polymerization. A mixture of α-fluoroacrylic methyl ester/ethylene glycoldimethacrylate/AIBN/Hexadecanol in a weight ratio 88/9/1/2 is dispersed in a 0.5 wt-% SDS aqueous solution using a Ultra-Turrax high-shear homogenizer. Temperature is set at 85° C. for 15 hours and then at 75° C. for another 5 hours whereupon a second stage monomer mixture composed of 25 parts of 11 dimethylaminodecylmethacrylate and 5 parts of divinylbenzene is metered together with 5 parts of a 5 wt-% aqueous solution of sodium persulfate. The dispersion is then cooled down to ambient temperature and treated with dimethylsulfate to convert the diamino groups in trimethylammonium sulfate groups. The suspension is further treated with HCl to convert the core methyl ester in the desired acid moieties. The average particle diameter is measured by a Malvern laser diffraction particle size at 0.5 micron.

H. Synthesis of Vinylphosphonate/Acrylic Acid Copolymer Beads

Vinylphosphonate and acrylic acid are first 50 mol-% neutralized with NaOH to form a 50 wt-% aqueous solution; to this mixture methylene-bis-acrylamide is added in a 10 wt-% to monomers. 100 parts of that monomer mixture are then emulsified in 200 parts of hexane and 1 part of sesquioleate sorbital as a surfactant. 10 parts of a 5 wt-% aqueous solution of sodium persulfate is further added to the suspension. The reaction is held @ 80 deg.C. for 10 hrs, while 10 parts of sodium persulfate solution are added. The water is then stripped off by a Dean-stark apparatus, the beads filtered and washed repeatedly by methanol and water in this order.

I. Synthesis of Vinylphosphonate/α-Fluoroacrylic Acid Copolymer Beads

The process described above in Example 2H is repeated except that acrylic acid is replaced by α-fluoroacrylic acid J. Synthesis of Polyvinylsulfate Beads Crosslinked polyvinylacetate beads are prepared by direct suspension polymerization, filtered, and hydrolyzed to polyvinylalcohol beads by basic hydrolysis in methanol/NaOH. After extensive washing, the beads are further treated with sulfur trioxide/trimethylamine to yield the desired polyvinylsulfate particles.

K. Synthesis of (poly-vinylphosphonate/acrylic acid)-core/(styrene-vinylpyridine)-Shell Using a Block Copolymer Approach A diblock copolymer is prepared that comprises a polyethyl acrylate block and a second block of a copolymer styrene/4-vinylpyridine in a 50:50 wt ratio; the block ratio is chosen at 1:1.5 and the overall molecular weight is 50,000 g/mol. Next, an emulsion process is carried out wherein 1 part of block copolymer is solubilized in 100 parts of de-ionized water to which is added 20 parts of a mixture composed of terbutyl-acrylate, ethyl-vinylphosphonate, ethylene glycol dimethacrylate, benzoyl peroxide in a 78:18:3:1 wt ratio. The temperature is raised to 70° C. and the reaction is allowed to proceed for 10 hours. Residual monomers are stripped off with a Dean-Stark device and particles are then boiled in 1M HCl overnight, neutralized with NaOH, water washed, and finally re-acidified with dilute HCl to yield the desired core-shell particles.

L. Preparation of Core-Shell Particles Comprising a Crosslinked Polyvinylsulfamate Core and a 11-dimethyl-aminodecylmethacrylate/laurylmethacrylate Copolymer Shell The shell polymer is prepared separately by free radical polymerization of a 50:50 wt ratio of 11-dimethyl-aminodecylmethacrylate/lauryl methacrylate monomer mixture at 20 wt-% in DMF using AIBN as an initiator. The beads obtained from Example 2B are spray-coated with the above-mentioned polymer shell solution using a Wurster fluid bed coater 2"-4"/6" Portable Unit. The fluidized bed unit is operated so that an average 5 microns thick coating is deposited on the core particles.

M. Core-Shell Particles Using a Latex Deposition Process

The shell polymer is prepared as an emulsion using either direct emulsification techniques or emulsion polymerization. The beads are then contacted with the latex for a given period of time, decanted, and spray dried. Higher shell deposition rates are achieved by inducing incipient coagulation of the latex on the core beads, by either changing the temperature, adding electrolyte, varying pH, or a combination thereof.

N. Core-Shell Particles Prepared from Poly α-Acrylic Acid Core Particles and Polyallylamine/Polystyrene Sulfonate Multilayer Shell Negatively charged core beads of Example 21 are first suspended in a dilute aqueous solution of poly(allylamine hydrochloride) at ambient temperature for 20 minutes and beads are separated from solution by centrifugation and subsequently washed with water. The beads are then suspended in a diluted aqueous solution of sodium polystyrenesulfonate for 20 minutes and separated by centrifugation and washed with water. This process is repeated until a 20 nm thick shell is obtained.

O. Polyacrylic Acid Core/Lactose Containing Shell Beads

A styrene derivative of lactose (glycomonomer) is prepared according to the procedure described by Kobayashi, et al, Macromolecules 1997, 30, 2016-2020. A glycopolymer is prepared by copolymerization of glycomonomer, glycidyl methacrylate, and butyl acrylate in DMF using AIBN as initiator. The glycopolymer is attached to poly(acrylic acid) beads by suspending the beads in glycopolymer solution in DMF at 60° C. for 8 hours and the core/shell beads are isolated by centrifugation and washed with DMF and water.

Example 3

Measurement of Sodium-Binding Capacity in Physiological Conditions Representative of the Upper GI Tract Particles of Examples 2A-2O are conditioned under the proton form and added to a reconstituted GI fluid representative of the jejunum segment, including bile acids, fatty acids, and intestinal enzymes. Na and K cations are set at 80 mM and 15 mM, respectively. After incubation at 37° C. for 30 minutes the beads are isolated by filtration and washed with de-ionized water. Then a 0.5 M LiCl solution is added to displace both Na and K cations. The cation binding capacity is then calculated and found in the range of 3 mmol/gr to 10 mmol/gr for sodium and 0.2 mmol/gr to 2 mmol/gr for potassium.

Measurement of Sodium-Binding Capacity in Physiological Conditions Representative of the Lower GI Tract Particles of Examples 2A-2O are incubated in the simulated upper tract fluid and isolated and washed as indicated above and are then added to a simulated fluid representative of the colon environment where potassium and sodium ions concentrations are set to 70 mM and 0 mM. After a 30 minute incubation, the particles are spun down and the supernatant assayed for Na released from the bead and resulting Na binding capacity computed. A comparative example is performed with a commercial polystyrene sulfonate resin in the acidic form with a 5 mmol/gr nominal capacity. All the particles of the present invention show superior binding of Na in both upper and lower tract simulated fluids.

Example 4

Animal Model to Demonstrate Non-Absorbed Nature of the Na-Binding Resin

These studies are done using single bolus administration of $^3$H- or $^{14}$C-labelled resin given to rats housed in metabolic chambers. The study design consists of two groups of six Sprague-Dawley rats; animals in group 1 receive a single oral dose of radiolabelled resin (250 mg/kg body weight), whereas animals in group 2 are pretreated with unlabelled resin in the diet at ~6 g/kg/day for 28 days, followed by a single administration of labeled resin on day 29 (250 mg/kg body weight). Group 1 is used to measure absorbance and clearance in resin-naïve animals, whereas Group 2 is used to monitor absorbance and clearance in chronically-treated animals, as might be seen in patients who take the resin on a daily basis. Total urine and feces are collected and analyzed for radiolabel at 0, 6, 12, 18, 24, 48, and 72 hours after administration of labeled resin. At sacrifice, aliquots of blood are removed and plasma harvested by centrifugation; the contents of the GI tract are collected and tissue samples from the stomach, caecum, small intestine, large intestine, rectum, liver, spleen, skeletal muscle, and lymph nodes are collected. Urine, tissue, and GI content weights are determined and tissue is minced. Radioactivity in urine and plasma is determined by liquid scintillation count. Fecal tissue and whole blood homogenates are aliquotted and combusted with radioactivity trapped in the water phase determined by liquid scintillation counting. Properties of a non-absorbed resin are: (i) no significant urinary excretion of radioactivity (<0.05% of the dose for both groups), (ii) mean total radioactivity excreted in the feces between 97%-100% of the total dose for both groups, recovered within the 72 hour collection period; (iii) blood, plasma, liver, kidney, spleen, skeletal muscle, and lymph node (i.e., non-gastrointestinal tissues) have <0.07% of total labeled resin dose at 72 hour collection point; and (iv) stomach, small intestine, large intestine, caecum, rectum have <0.1% total dose of labeled resin at 72 hour collection point.

Example 5

Human Volunteer Studies to Demonstrate Non-Absorbed Nature of the Na-Binding Resin 14C-labelled resin is prepared to give roughly 0.2 mCi/g of resin. In a typical study design, twenty volunteers receive 3×600 mg capsules of unlabelled resin three times a day for 28 days (total daily dose=5400 mg). Sixteen subjects are admitted to the clinical research metabolic unit at a designated center, to continue with the radiolabel portion of the study. On the morning of the first confinement day, the subjects receive a single oral 2.4 g dose (4×600 mg capsules) of 14C-labelled resin for a total of 480 uCi of 14C per subject. Unlabelled resin is then administered as before over the next three days. Blood samples are drawn at 0, 4, 8, 12, 24, 48, 72, and 96 hours. Voided urine and feces are collected at baseline over the intervals 0-24 hr, 24-48 hr, 48-72 hr, 72-96 hr. Homogenized fecal and whole blood samples are dried and oxidized prior to scintillation counting. Radioactivity in the blood, urine, and feces is expressed as a percentage of the administered dose for each time interval and as a total percentage. Properties of a non-absorbed resin are: (i) no detectable amounts of 14C-resin in the whole blood of any subject at any time during the study; (ii) for each subject, <0.009% of the labeled-resin dose in the collected urine samples, covering the 96 hour period following administration of the labeled-resin; and (iii) for each subject, >99% of the dose is recovered in the feces over a 10 day period following 14C-resin administration.

Example 6

Animal Models to Demonstrate Na-Binding Capacity of Resins

Animal models are used to demonstrate the binding of sodium cations by the resins, which are supplemented into a controlled diet administered to rats or dogs. These studies generally are conducted in normal animals to demonstrate an effect of the resin, then in diseased animal models where a sustained imbalance of electrolytes leading to extravascular edema is created by compromising the kidney, liver, or cardiac function of the test animal.

A typical experiment with normal rats to determine relative binding efficiency of the test polymers uses three groups (n=6/group) of Sprague-Dawley female rats placed in single metabolic cages on a diet consisting of low-sodium biscuits and distilled water. Sodium is administered daily via oral feeding tube in three doses as a 200 mM solution (2.4 mEq). During the first three days of the test, baseline data is collected in the form of mEq/day of sodium in the urine and mEq/day of sodium in feces; usual sodium measures are 2.25-2.5 mEq/day in urine and 0.05-0.3 mEq/day in feces. In the next three days, the three groups of test animals receive fixed doses of the test resin (500, 1000, 2000 mg/kg/d) in addition to the saline solution administered by oral gavage over three doses. In the final three days of the test, the resin is removed from the oral gavage and saline solution is administered as in the first period to provide a second, follow-up control period. Active resins are those that decrease sodium in the urine during the second dosing period below 2.25 mEq/day (typical ranges are 0.25-1.5 mEq/day) and increase the sodium content of the feces (typical values range from 2 mEq/g-5 mEq/g of resin). Sodium content in urine and feces is determined by extraction and ion exchange chromatography or by flame photometry.

A typical experiment with rats that have compromised kidney function, used to mimic hypertension and fluid retention in the ESRD patient, uses chemical induction of kidney damage (uranyl acetate, gentamicin, cephaloradine, etc) or surgical resection of the kidney (5/6ths nephrectomy) to induce chronic renal failure. After the chemical or surgical manipulation of the animals and stabilization of renal function at a reduced state, the animals are divided into three test groups (n=10/group). As in the normal animal tests, the test animals are maintained for 3 days on low-sodium biscuits and receive 75 mM NaCl solution ad lib; baseline sodium values are determined for urine and feces. The animals in each group are then given fixed amounts of the resin by oral gavage (3 doses, total daily doses of 500, 1000, and 2000 mg/kg/d) for three days, with a "washout" period for three days following resin dosing. Sodium in urine and feces is determined throughout the baseline, test and washout periods; sodium content in the urine is generally elevated in the baseline and washout periods (4-5 mEq/d), but is reduced in the treatment phase (1-2 mEq/d). Similarly, fecal sodium in the baseline and washout groups is 0.03-0.5 mEq/d and increases to 3.8-5 mEq/g of resin in the treated animals.

Example 7

Human Volunteer Studies to Demonstrate Sodium-Binding Capacity of Resins

Completion of IND-enabling safety pharmacology and toxicology analysis of the resins will allow human volunteer studies in normal subjects, to evaluate the in vivo binding capacity of the test resins. The design of a typical study enrolls 24 normal subjects housed in a clinical metabolic unit; the subjects have normal body weight, hematology and chemistry tests and have no history of GI, renal or hepatic disease. After screening, the volunteers are randomized into 3 groups of 8 subjects each; six of the subjects in each group are randomized to receive a specific dose of resin (25 mg/kg; 70 mg/kg; 140 mg/kg) and two receive placebo. The volunteers are housed on the metabolic unit for 18 days and consume a sodium-controlled diet of 5 g elemental sodium per day (3 meals plus 1 snack). The study design is as follows; on day 1, the subjects receive a single oral dose of resin or placebo according to treatment group. For the next seven days (d2-d8) the subjects receive no drug; from the morning of day 5 to the morning of day 9, 24 hr urine and feces are collected and the sodium and potassium content of the samples determined. On days 9-16, all subjects receive the same dosing according to group, with the doses divided over three daily doses; total urine and feces are collected from day 13 through day 17. The subjects are discharged on day 18. Fecal sodium content is elevated in the treatment groups, approaching 4-5 mEq/g resin.

Example 8 pH Triggered Membrane

Figure 2:
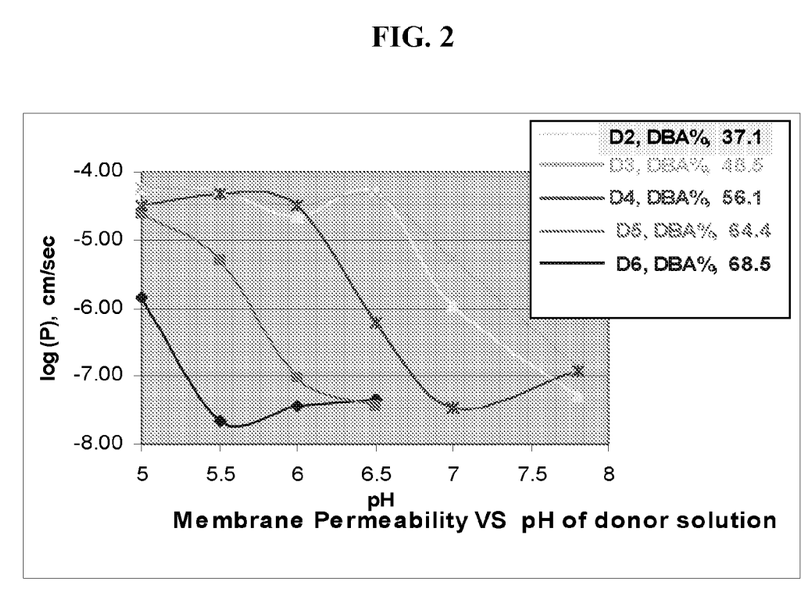
FIG. 2 depicts membrane permeability to sodium at different pHs.

Membranes with co-polymers of dibutyl acrylamide, and dimethyl aminoethyl methacrylate were synthesized and their permeability profiles were evaluated at different pHs. Donor solution used to study permeability was 50 mM of $Na^+$ buffer at different pHs. The results are depicted in FIG. 2. With increasing pH (pH range 5-8), the membrane permeability decreased and even became impermeable at a high pH. The composition of the membrane also affected the permeability. For samples with DBA<50% (D2, D3), membrane was impermeable at high pH (>7.5).

All publications and patent applications mentioned in this specification are herein incorporated by reference to the same extent as if each individual publication or patent application was specifically and individually indicated to be incorporated by reference.

It will be apparent to one of ordinary skill in the art that many changes and modifications can be made thereto without departing from the spirit or scope of the appended claims.

What is claimed is:

1. A method of removing sodium from an animal subject comprising administering to an animal subject in need thereof an effective amount of a core-shell composition comprising a cation exchange core and a semi-permeable shell wherein the semi-permeable shell comprises a polymer containing at least one of a poly-11 trimethylammonioundecylmethacrylate polymer, or a 11-dimethyl-aminodecylmethacrylate/lauryl-methacrylate copolymer, wherein said semi-permeable shell has a high permeability to sodium in the duodenum where the shell is in a hydrated state at neutral pH and has a reduced permeability to sodium in the cecum and colon where it is in a collapsed-impermeable state when the pH is 5 or 6, whereby as the core-shell composition passes from the duodenum to the cecum and colon its permeability to sodium decreases.

2. The method of claim 1 wherein said animal subject is suffering from hypertension, chronic heart failure, end stage renal disease, liver cirrhosis, chronic renal insufficiency, fluid overload, or sodium overload.

3. The method of claim 1 wherein extra cellular water is removed from said animal subject.

4. The method of claim 1 wherein a beneficial effect is observed on fluid management, blood pressure control, and/or interdialytic weight gain.

5. The method of claim 1 wherein said animal subject is suffering from a disease characterized by a presence of abnormal quantities of sodium and/or water in the body of said animal subject.

6. The method of claim 1 wherein said animal subject is resistant to diuretic treatment and is suffering from hypertension, chronic heart failure, end stage renal disease, liver cirrhosis, chronic renal insufficiency, fluid overload, or a combination thereof.

7. The method of claim 1 wherein treatment of said animal subject reduces formation of edema after a cardiac event.

8. The method of claim 1 wherein said animal subject is suffering from volume/salt sensitive diastolic heart failure.

9. The method of claim 1 wherein said composition is co-administered with a diuretic, an angiotensin converting enzyme (ACE) inhibitor, an α-blocker, a β-blocker, an angiotensin II receptor blocker, or a combination thereof.

10. The method of claim 1 wherein said composition is co-administered with a laxative.

11. The method of claim 1, said cation exchange core being capable of binding sodium in an upper gastro-intestinal tract and the semi-permeable shell being characterized by decreased permeability to the bound sodium in a lower gastro-intestinal tract relative to the permeability exhibited by the core-shell composition to said bound sodium in the upper gastrointestinal tract.

12. The method of claim 11 wherein said composition is co-administered with a diuretic, an angiotensin converting enzyme (ACE) inhibitor, an α-blocker, a β-blocker, an angiotensin II receptor blocker, or a combination thereof.

13. The method of claim 1 wherein said cation exchange core comprises a structural unit selected from the group consisting of 14. The method of claim 13, said cation exchange core being capable of binding sodium in an upper gastro-intestinal tract and the semi-permeable shell being characterized by decreased permeability to the bound sodium in a lower gastro-intestinal tract relative to the permeability exhibited to said bound sodium in the upper gastrointestinal tract.

15. The method of claim 1 wherein the semi-permeable shell comprises the poly-11 trimethylammonioundecylmethacrylate polymer.

16. The method of claim 1 wherein the semi-permeable shell comprises the 11-dimethyl-aminodecylmethacrylate/laurylmethacrylate copolymer.

* * * * *